United States Patent
Gutterer

(10) Patent No.: US 6,787,533 B1
(45) Date of Patent: Sep. 7, 2004

(54) PROCESS FOR R-EPIMER ENRICHMENT OF 16,17-ACETAL DERIVATIVES OF 21-ACYLOXY PREGNA,4-DIEN-11.BETA., 16.ALPHA., 17.ALPHA.-TRIOL-3,20-DIONE DERIVATIVES

(75) Inventor: Beate Gutterer, Allensbach (DE)

(73) Assignee: Altana Pharma AG, Constance (DE)

( * ) Notice: Subject to any disclaimer, the term of this patent is extended or adjusted under 35 U.S.C. 154(b) by 513 days.

(21) Appl. No.: 09/147,675

(22) PCT Filed: Aug. 29, 1997

(86) PCT No.: PCT/EP97/04716

§ 371 (c)(1),
(2), (4) Date: Feb. 11, 1999

(87) PCT Pub. No.: WO98/09982

PCT Pub. Date: Mar. 12, 1998

(30) Foreign Application Priority Data

Sep. 3, 1996 (DE) .......................... 196 35 498

(51) Int. Cl.[7] .............................. A61K 31/58; C07J 71/00
(52) U.S. Cl. .......................................... 514/174; 540/63
(58) Field of Search ............................ 514/174; 540/63

(56) References Cited

U.S. PATENT DOCUMENTS

| 3,928,326 | A | * | 12/1975 | Brattsand et al. | ...... 260/239.55 |
| 3,992,534 | A | * | 11/1976 | Brattsand et al. | ........... 424/241 |
| 3,996,359 | A | * | 12/1976 | Brattsand et al. | ........... 424/241 |
| 4,036,831 | A | * | 7/1977 | Loken et al. | ....... 260/239.55 R |
| 4,695,625 | A | * | 9/1987 | MacDonald | ................ 540/63 |
| 4,835,145 | A | * | 5/1989 | MacDonald | ................ 514/174 |
| 5,482,934 | A | | 1/1996 | Calatayud et al. | .......... 514/174 |
| 5,482,935 | A | | 1/1996 | Adelman et al. | ........... 514/182 |
| 5,728,826 | A | | 3/1998 | Gutterer | ...................... 540/61 |
| 5,733,901 | A | | 3/1998 | Gutterer | ..................... 514/174 |

OTHER PUBLICATIONS

Linus Pauling (Genral Chemistry, W.H. Freeman and Company, San Francisco, California (1947), Chapter 2, p. 14, last para and p. 15 lines 1–2)., 1947.*
Acta Pharmaceutica Suecicia, vol. 24, pp. 97–114, (1987).

* cited by examiner

Primary Examiner—Thurman K. Page
(74) Attorney, Agent, or Firm—Jacobson Holman PLLC

(57) ABSTRACT

R-epimer enrichment of 16,17-acetal derivatives of 21-acyloxy pregna-1,4-dien-11beta,16alpha,17alpha-triol-3,20-dione derivatives is effected by fractional crystallization.

17 Claims, No Drawings

PROCESS FOR R-EPIMER ENRICHMENT OF 16,17-ACETAL DERIVATIVES OF 21-ACYLOXY PREGNA,4-DIEN-11.BETA., 16.ALPHA., 17.ALPHA.-TRIOL-3,20-DIONE DERIVATIVES

FIELD OF THE INVENTION

The invention relates to a novel process for increasing the proportion of one epimer in epimer mixtures of certain pregna-1,4-diene-3,20-dione 16,17-acetal 21-esters.

PRIOR ART

DE-A 41 29 535 discloses epimeric pregna-1,4-diene-3, 20-dione 16,17-acetal 21-esters with an antiinflammatory action. These have a butyl, isopropyl, sec-butyl, cyclohexyl or phenyl radical on the cyclic acetal ring, and their C-21 hydroxyl group is acylated by an acetyl or isobutyryl radical. The application describes how the respective R-epimer is obtained, starting from an R/S mixture, by preparative high-pressure liquid chromatography (HPLC). International Patent Application WO95/24416 describes a process for the epimer enrichment of pregna-1,4-diene-3,20-dione 16,17-acetal derivatives by silylation, fractional crystallization and acid hydrolysis.

DESCRIPTION OF THE INVENTION

In the case of active ingredients having one or more chiral centers, one stereoisomer, for example an epimer, is often more effective or associated with fewer side effects than the other. Obtaining the desired stereoisomer as selectively and purely as possible is therefore of great importance for chiral active ingredients.

According to the invention, a novel process is provided which, surprisingly, permits the separation of the epimers of certain pregna-1,4-diene-3,20-dione 16,17-acetal 21-esters.

The invention relates to a process for increasing the proportion of the R-epimer in an R/S-epimer mixture of compounds of the formula I (see attached formula sheet), where R1 is 1–7C-alkyl or 3–8C-cycloalkyl and R2 is 1–7C-alkylcarbonyl or 3–8C-cycloalkylcarbonyl, which comprises subjecting the R/S-epimer mixture of the compounds of the formula I to fractional crystallization.

This fractional crystallization, which can also be repeated if necessary, permits, according to the invention, the R-epimer proportion to be increased to >97%, in particular to >99%. 1–7C-Alkyl is straight-chain or branched alkyl radicals having 1 to 7 carbon atoms. Examples which may be mentioned are the heptyl, hexyl, neopentyl, isopentyl, pentyl, butyl, iso-butyl, sec-butyl, tert-butyl, propyl, isopropyl, ethyl and methyl radicals.

A preferred 1–7C-alkyl radical R1 is the propyl radical.

3–8C-Cycloalkyl is the cyclopropyl, cyclobutyl, cyclopentyl, cyclohexyl, cycloheptyl or cyclooctyl radical. A preferred 3–8C-cycloalkyl radical R1 is the cyclohexyl radical.

1–7C-Alkylcarbonyl is a carbonyl group to which one of the aforementioned 1–7C-alkyl radicals is bonded. Examples which may be mentioned are the acetyl, propionyl, butyryl, pentanoyl and, preferably, isobutyryl radicals.

3–8C-Cycloalkylcarbonyl is a carbonyl group to which one of the aforementioned 3–8C-cycloalkyl radicals is bonded. The cyclohexylcarbonyl radical is preferred.

A particularly preferred embodiment of the process according to the invention is increasing the proportion of the R-epimer in an R/S-epimer mixture of compounds of the formula I in which R1 is cyclohexyl and R2 is isobutyryl, which has the chemical name [11beta, 16alpha (R,S)]-16, 17-[(cyclohexylmethylene)bis(oxy)]-11-hydroxy-21-(2-methyl-1-oxopropoxy)-pregna-1,4-diene-3,20-dione.

The fractional crystallization of the R/S-epimer mixture of the formula I is advantageously carried out from a solution of the R/S-epimer mixture of the formula I in a mixture of water and a suitable, water-miscible organic solvent.

The process according to the invention is carried out by dissolving the R/S-epimer mixture of the formula I in a suitable, water-miscible organic solvent, expediently at elevated temperature, in particular at the boiling point of the solvent used. The subsequent addition of water is expediently carried out with stirring and whilst maintaining the elevated temperature, in particular at the boiling point; after the water has been added, the mixture Is cooled, preferably to room temperature, with vigorous stirring (in order to obtain as finely crystalline a product as possible).

Alternatively, the R/S-epimer mixture of the formula I can be suspended in a mixture of water and a suitable, water-miscible organic solvent and dissolved by heating, in particular to the boiling point of the solvent mixture. The solution is then cooled, preferably to room temperature, with vigorous stirring.

Cooling is advantageously carried out slowly, preferably over a period of from 2 to 10 hours.

The subsequent fractional crystallization can advantageously be influenced by adding seed crystals, preferably those of the respective pure R-epimer of the formula I.

Examples of suitable, water-miscible organic solvents which may be mentioned are acetone or in particular alcohols, such as isopropanol, n-propanol, methanol and preferably ethanol, and their mixtures in any mixing ratio. To dissolve 0.18 mol of R/S-epimer mixture of the formula I, 190–700 ml of the suitable water-miscible organic solvent, preferably 300–400 ml, are expediently used. The volume ratio of the water to the water-miscible organic solvent is preferably in the range 0.1–1 [v/v], in particular 0.25–0.75 [v/v].

The R-epimer-enriched R/S-epimer mixture of the formula I is then removed from the solution in a manner known to the person skilled in the art, in particular by filtration.

In implementing the process according to the invention, it is advantageous to start from those compounds of the formula I in which the proportion of the R-epimer has already been increased, for example the content of R-epimer is $\geq 75\%$, in particular $\geq 85\%$. The compounds of the formula I are obtained in a manner known per se, for example as described in DE-A 41 29 535. Alternatively, compounds of the formula I where R1 and R2 are as defined above can also be synthesized by acylation, starting from corresponding compounds of the formula I where R2 is hydrogen. Such starting compounds are described for example in WO95/24416. Acylation is carried out in a manner known to the person skilled in the art, e.g. as described in the examples.

The following examples describe the invention in more detail. RT stands for room temperature, min for minute(s), h for hour(s), m.p. for melting point and abs. for absolute.

EXAMPLES 1. 316 g (584 mmol) of [11beta, 16alpha (R,S)]-16,17-[(cyclohexylmethylene)bis(oxy)]-11-hydroxy-21-(2- methyl-1-oxopropoxy)-pregna-1,4-diene-3,20-dione, referred to as A hereinafter, (crude product, oil, R/S epimer ratio approximately 90/10) are dissolved in 1.1 l of abs. ethanol, and 700 ml of water are added to the boiling mixture. The mixture is allowed to cool to RT with vigorous stirring, and the precipitate is filtered off with suction, washed with 500 ml of abs. ethanol/water 2/1 and dried for 5 h at 50° C. in a vacuum drying cabinet.

Yield: 237 g (438 mmol, 75%) of A, R/S epimer ratio approximately 95/5. m.p.: 199–201° C.

The product is dissolved in 900 ml of abs. ethanol; 650 ml of water are added to the boiling mixture, and the product is isolated as given above.

Yield: 209 g (386.5 mmol, 88%) of A, R/S epimer ratio approximately 97/3. m.p.: 201–203° C.

The product is dissolved in 800 ml of abs. ethanol; 450 ml of water are added to the boiling mixture, and the product is isolated as given above.

Yield: 178 g (329 mmol, 85%) of A, R/S epimer ratio approximately 98.5/1.5. m.p.: 205–206° C.

The product is dissolved in 600 ml of abs. ethanol; 350 ml of water are added to the boiling mixture, and the product is isolated as given above.

Yield: 161 g (298 mmol, 90.5%) of A, R/S epimer ratio >99.5/0.5. m.p.: 206.5–207° C.

2. 1.5 g (2.77 mmol) of A (R/S epimer ratio approximately 89/11) are dissolved in 3 ml of abs. methanol, and 1 ml of water is added to the boiling mixture. The mixture is allowed to cool to RT with stirring, and the precipitate is filtered off with suction, rinsed with a little methanol/water 3/1 and dried as above.

Yield: 1.21 g (80.6%) of A, R/S epimer ratio approximately 93:7.

3. 5 g (9.25 mmol) of A (R/S epimer ratio approximately 91.5/8.5) are dissolved, with boiling, in 15 ml of isopropanol, and 10 ml of water are added to the mixture. The mixture is allowed to cool to RT with stirring, and the precipitate is filtered off with suction, rinsed with a little isopropanol/water 2/1 and dried as above.

Yield: 4 g (80%) of A, epimer ratio R/S approximately 94/6.

4. 1.5 g (2.77 mmol) of A (R/S epimer ratio approximately 89/11) are dissolved, with boiling, in 4 ml of acetone, and 1 ml of water is added. The mixture is allowed to cool to RT with stirring, and the precipitate is filtered off with suction, rinsed with a little acetone/water 2/1 and dried as above.

Yield: 1.12 g (75%) of A, R/S epimer ratio approximately 95/5.

Preparation of the Starting Compounds of the Formula I

A: [11beta, 16alpha (R,S)]-16,17-[(Cyclohexylmethylene)bis(oxy)]-11-hydroxy-21-(2-methyl-1-oxopropoxy)-pregna-1,4-diene-3,20-dione 10 g of [11beta, 16alpha (R,S)]-16,17-[(cyclohexylmethylene)bis(oxy)]-11,21-dihydroxypregna-1,4-diene-3,20-dione and 6 g of potassium carbonate are suspended in 50 ml of acetone; 4.4 ml of isobutyric anhydride are added with stirring, and the suspension is refluxed for 2.5 h. After the mixture has cooled to RT, 100 ml of water are slowly added to the suspension. The product is filtered off with suction, washed with water and dried. The R-epimer proportion is increased as described above.

Yield of crude product: 11.4 g (99.3% of theory) of [11beta, 16alpha (R,S)]-16,17-[(cyclohexylmethylene)bis(oxy)]-11-hydroxy-21-(2-methyl-1-oxopropoxy)-pregna-1,4-diene-3,20-dione.

Determination of the epimer ratios for compounds of the formula I

The epimer ratios are determined by HPLC.

| HPLC conditions: | |
|---|---|
| Column material: | Hypersil C18, 5 μm, 125 × 4.6 mm |
| Detector wavelength: | 242 nm |
| Sample concentration: | 0.5–1.5 mg/ml |
| Sample volume: | 20 μl |
| Flow rate: | 1 ml/min |
| Oven temperature: | 20° C. |
| Compound A: | eluent water (45%)/ethanol (55%) |

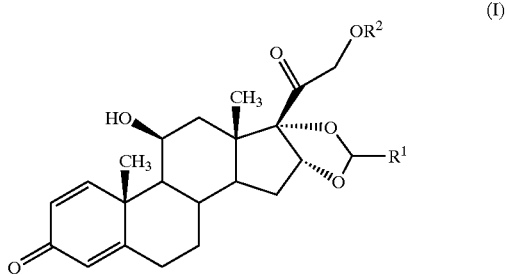

(I)

What is claimed is:

1. A process for increasing the proportion of R-epimer in an R/S-epimer mixture of compounds of formula I

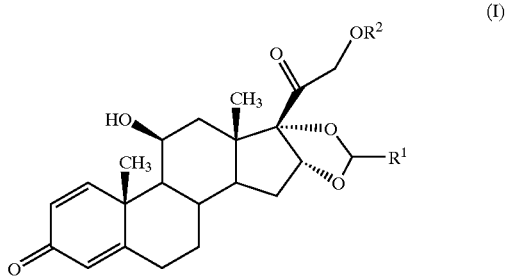

(I)

wherein R1 is 3–8C-cycloalkyl and R2 is 1–7C-alkylcarbonyl or 3–8C-cycloalkylcarbonyl, which comprises subjecting the R/S-epimer mixture of the compounds of formula I to fractional crystallization carried out from a solution of the R/S-epimer mixture of formula I in a mixture of water and a suitable, water-miscible organic solvent.

2. A process as claimed in claim 1 wherein R2 is 1–7C-alkylcarbonyl.

3. A process as claimed in claim 1 wherein R2 is 3–8C-cycloalkylcarbonyl.

4. A process as claimed in claim 1, wherein the R/S-epimer mixture of compounds of formula I has the chemical name [11beta, 16alpha (R,S)]16,17-[(cyclohexylmethylene)bis(oxy)]-11-hydroxy-21-(2-methyl-1-oxopropoxy)-pregna-1,4-diene-3,20-dione.

5. A process as claimed in claim 1 wherein the proportion of the R-epimer in the R/S-epimer mixture of compounds of formula I subjected to fractional crystallization is at least 75%.

6. A process as claimed in claim 1, wherein the suitable, water-miscible organic solvent is ethanol.

7. A process as claimed in claim 1, wherein the suitable, water-miscible organic solvent is methanol, n-propanol, isopropanol or acetone.

8. A process as claimed in claim 1, wherein the suitable, water-miscible organic solvent is a mixture of organic solvents.

9. A process for the production of an R/S-epimer mixture of [11 beta, 16 alpha (R,S)]-16,17-[(cyclohexylmethylene) bis(oxy)]-11-hydroxy-21-(2-methyl-1-oxopropoxy)-pregna-1,4-diene-3,20-dione and for increasing the proportion of the R-epimer in the mixture, which comprises the steps of (a) subjecting an R/S-epimer mixture of [11 beta, 16 alpha (R,S)]-16,17-[(cyclohexylmethylene)bis(oxy)]-11,21-dihydroxypregna-1,4-diene-3,20-dione to acylation and (b) subjecting the R/S-epimer mixture obtained in step (a) to fractional crystallization in a mixture of water and a suitable, water-miscible organic solvent.

10. A process of claim 9 wherein acylation is effected with isobutyric anhydride.

11. A process of claim 9 wherein the mixture of water and a suitable, water-miscible solvent has a volume ratio of the water to the water-miscible organic solvent in the range of from 0.1 to 1 (v/v).

12. A process of claim 11 wherein the ratio is from 0.25 to 0.75.

13. A process of claim 9 which comprises increasing the proportion of the R-epimer in the mixture to at least 75%.

14. A process of claim 13 wherein the content of R-epimer is increased to at least 85%.

15. A process of claim 9 wherein the suitable, water-miscible organic solvent is ethanol.

16. A process of claim 9 wherein the suitable, water-miscible organic solvent is methanol, n-propanol, isopropanol or acetone.

17. A process of claim 9 wherein the suitable, water-miscible organic solvent is a mixture of organic solvents.

* * * * *